(12) United States Patent
Yang et al.

(10) Patent No.: US 8,114,336 B2
(45) Date of Patent: Feb. 14, 2012

(54) METHODS FOR INCREASING THE STRENGTH AND CONTROLLING THE ARCHITECTURE AND COMPOSITION OF CERAMIC ARTICLES

(75) Inventors: Yunzhi Yang, Memphis, TN (US); Yongxing Liu, New Britain, CT (US)

(73) Assignee: Board Of Regents Of The University Of Texas System, Austin, TX (US)

( * ) Notice: Subject to any disclaimer, the term of this patent is extended or adjusted under 35 U.S.C. 154(b) by 530 days.

(21) Appl. No.: 12/074,434

(22) Filed: Mar. 4, 2008

(65) Prior Publication Data

US 2008/0226893 A1 Sep. 18, 2008

Related U.S. Application Data

(60) Provisional application No. 60/918,434, filed on Mar. 16, 2007.

(51) Int. Cl.
*C04B 38/04* (2006.01)
(52) U.S. Cl. .................. 264/656; 264/657; 264/344
(58) Field of Classification Search .............. 264/86, 264/651, 654, 656, 657, 628, 344
See application file for complete search history.

(56) References Cited

U.S. PATENT DOCUMENTS

| | | | |
|---|---|---|---|
| 2,939,199 A | 6/1960 | Strivens | |
| 4,197,118 A * | 4/1980 | Wiech, Jr. ................ | 75/228 |
| 4,327,065 A | 4/1982 | Von Dardel et al. | |
| 4,404,166 A * | 9/1983 | Wiech, Jr. ................ | 419/36 |
| 4,731,208 A * | 3/1988 | Nakajima et al. ......... | 264/37.13 |
| 4,996,024 A * | 2/1991 | Nishio et al. ............. | 419/40 |
| 5,059,388 A * | 10/1991 | Kihara et al. ............ | 419/37 |
| 5,332,537 A * | 7/1994 | Hens et al. ............... | 264/496 |
| 5,525,557 A | 6/1996 | Pujari et al. | |
| 5,877,270 A * | 3/1999 | Takayama et al. ....... | 264/344 |
| 5,885,493 A * | 3/1999 | Janney et al. ............ | 264/37.18 |
| 6,368,703 B1 | 4/2002 | Johnson | |
| 6,451,059 B1 | 9/2002 | Janas et al. | |
| 6,673,285 B2 | 1/2004 | Ma | |
| 7,094,371 B2 | 8/2006 | Lo | |
| 7,163,651 B2 * | 1/2007 | Chern Lin et al. ....... | 264/42 |
| 2002/0037799 A1* | 3/2002 | Li et al. ................... | 501/82 |
| 2003/0114936 A1 | 6/2003 | Sherwood | |
| 2005/0209704 A1 | 9/2005 | Maspero et al. | |
| 2006/0024500 A1* | 2/2006 | Seo ........................... | 428/402 |
| 2007/0228621 A1* | 10/2007 | Sachs et al. .............. | 264/638 |

OTHER PUBLICATIONS

Zollfrank, C. et al., "Biomorphous SiOC/C-ceramic composites from chemically modified wood templates," Journal of the European Ceramic Society, 24, 2004, pp. 479-487.
International Search Report for International Application No. PCT/US09/03501, dated Aug. 11, 2009, 1 page.
Liu, DM, "Influence of Porosity and Pore Size on the Compressive Strength of Porous Hydroxyapatite Ceramic", Ceramics International, 23:135-139 (1997).

(Continued)

*Primary Examiner* — Joseph Del Sole
*Assistant Examiner* — Ryan Ochylski
(74) *Attorney, Agent, or Firm* — Conley Rose, P.C.

(57) ABSTRACT

Ceramic porous and non-porous articles are made by a process that includes a hardening step in which a fluid-containing ceramic composition is exposed to a solvent in which the fluid in the composition is soluble before the ceramic composition is solidified into the final ceramic article.

16 Claims, 4 Drawing Sheets

OTHER PUBLICATIONS

Milosevski, M, et al, "Preparation and Properties of Dense and Porous Calcium Phosphate", Ceramics International, 25:693-696 (1999).

Sepulveda, P, et al, "Production of Porous Hydroxyapatite by the Gel-Casting of Foams and Cytotoxic Evaluation", J. Biomed. Mater. Res., 50:27-34 (2000).

Sous, M, et al, "Cellular Biocompatibility and Resistance to Compression of Macroporous Beta-tricalcium Phosphate Ceramics", Biomaterials, 19:2147-2153 (1998).

Studart, AR, et al, "Processing Routes to Macroporous Ceramics: A Review", J. Am. Ceram. Soc., 89(6):1771-1789 (2006).

Williams, JM, et al, "Bone Tissue Engineering Using Polycaprolactone Scaffolds Fabricated via Selective Laser Sintering", Biomaterials, 26:4817-4827 (2005).

Wong, LH, et al, "Functionally Graded Tricalcium Phosphate/Fluoroapatite Composites", Materials Science and Engineering, C20:111-115 (2002).

* cited by examiner

METHODS FOR INCREASING THE STRENGTH AND CONTROLLING THE ARCHITECTURE AND COMPOSITION OF CERAMIC ARTICLES

This application claims the benefit of U.S. Provisional Patent Application 60/918,434, which was filed on Mar. 16, 2007.

FIELD OF THE INVENTION

The present invention pertains to the field of fabricating ceramic articles and particularly to the field of fabricating porous ceramic articles which may be used for various purposes, such as a scaffolding for many different applications, such as for tissue engineering.

BACKGROUND OF THE INVENTION

Ceramics are used extensively in a large number of industrial applications. They are used as building materials, as cements and mortars, as abrasives, and in recent years ceramics have been developed for specialized uses in such fields as electronics, communications, and medicine.

In medicine, biodegradable macroporous ceramic scaffolds have been used as engineered grafts for tissue engineering, particularly bone tissue engineering. Such scaffolds typically are made with hydroxyapatite (HA) or tricalcium phosphate (TCP), or a combination of HA and TCP, with additives such as silica, magnesium, sodium, potassium, and zinc. The porous nature of these scaffolds permits the ingrowth of vascular and structural tissues and, because the scaffolds are biodegradable, can be used safely and without the need to remove the implant from the body.

For bone repair, particularly for defects in the spine and long bones, such as the bones of the legs, it is critically important that a ceramic scaffold implant have a high compressive strength and that this strength is maintained as the implant is biodegraded before the bone itself has healed and has sufficient strength. However, there is an inverse relationship between porosity and mechanical strength of the implants as the mechanical strength decreases as the porosity and pore size increases. In addition, biodegradable synthetic bone implants decrease in strength as the implant is degraded by contact with body fluids. Loss of strength of an implant at a time before the healed bone is able to support weight or support itself can lead to failure of the implant and of the repair process.

Ma, U.S. Pat. No. 6,673,285 discloses a method for fabrication of porous articles, such as polymer scaffolds. Ma discloses that the scaffolds may be made by casting a composition onto a negative replica of a desired macroporous architecture of the porous article to form a body, and that the negative replica, referred to as a porogen, is removed, thereby forming the porous article. Ma discloses that this method may be utilized to form a porous article from various materials, including polymers, ceramics, glass, and inorganic compounds.

The inventors have utilized the method of Ma in order to attempt to make macroporous ceramic calcium phosphate (CaP) scaffolds. Such attempts, however, were unsuccessful and this process could not be used to form a sintered integrated ceramic body. It was found that the ceramic article produced in this manner lacked sufficient hardness and strength and broke into a multiplicity of pieces before and during sintering.

Various scientific articles describe methods of manufacture of macroporous ceramic (CaP) scaffolds of various porosity and report on the compressive strength of these scaffolds. See, Hing, J. Mater. Sci. Mater. Med., 10(3):135-145 (1999); Liu, Ceramics International, 23:135-139 (1997); Seplveda, J. Biomed. Mater. Res., 50:27-34 (2000); Ramay, Biomaterials, 24:3293-3302 (2003); Almirall, Biomaterials, 25:3671-3680 (2004); Cyster, Biomaterials, 26:697-702 (2005); Silva, Biomaterials, 27:5909-5917 (2006); Uemura, Biomaterials, 24:2277-2286 (2003); Sous, Biomaterials, 19:2147-2153 (1998); Guo, Tissue Engineering, 10:1830-1840 (2004); Kwon, J. Am. Ceramic Soc., 85:3129-3131 (2002); and Milosevski, Ceramics International, 25:693-696 (1999). These reports show that the strength of porous CaP scaffolds tends to decrease with increasing porosity and that most of the scaffolds produced by the prior art methods have a compressive strength of only about 0.8 to 8 MPa (megapascals) with one report of a scaffold having 70% porosity, pores not completely interconnected, and a compressive strength of about 11 Mpa.

A significant need exists for a method by which the compressive strength of ceramic articles may be increased. Such a need is critical for ceramic articles, such as synthetic bone grafts, that are intended to be weight bearing, and is especially critical for making ceramic articles that have intercommunicating pores throughout their structures.

DESCRIPTION OF THE INVENTION

Figure 1:
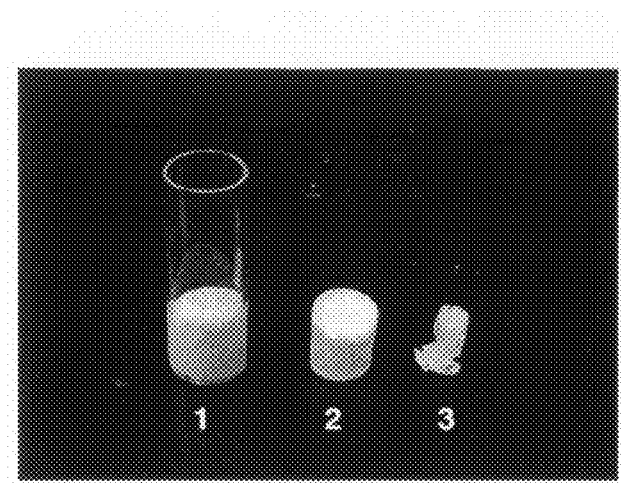
FIG. 1 is a photograph showing, on the left side, a ceramic composition slurry in a plastic tube container prior to drying, in the middle, a green body dried by the solvent extraction step of the method of the present invention, and on the right side, a green body dried by exposure to air at room temperature without the solvent extraction step of the invention.

The present invention is based upon the discovery by the inventors that removing liquid by solvent extraction from a fluid ceramic composition followed by solidifying the dried ceramic composition, such as by the application of heat, results in a ceramic article possessing unexpectedly higher strength than that possessed by similar ceramic articles that are made without the solvent-based liquid removal step.

The present invention permits the manufacture of strong ceramic articles for use in various industries, such as for building construction, electronics, telecommunications, and in the manufacture of housewares. The present invention is especially useful in the manufacture of biodegradable materials such as for implantation into the body, such as for porous implants such as those used for bone reconstruction and regeneration techniques.

In one embodiment, the invention is a method for making a ceramic article. According to this embodiment of the invention, a fluid ceramic composition is formed into a desired shape and is exposed to a solvent in which liquid contained in the ceramic composition is soluble at a concentration and for a time sufficient to extract some, a majority of, or all of the liquid from the composition. Following the extraction, the "dried" composition, which is preferably completely free of liquid, is caused or permitted to solidify to form a ceramic article.

In another embodiment, the invention is a ceramic article made by the method of the invention. Such a ceramic article may be referred to herein as "solvent-hardened", which term indicates that, prior to solidifying to form the ceramic article, the fluid ceramic composition that was used to make the article was exposed to a solvent in which liquid in the composition was soluble at a concentration and for a time sufficient to extract the liquid from the composition and, following this extraction, the composition was caused or permitted to solidify to form the solvent-hardened ceramic article.

As used herein, the term "ceramic material" refers to an inorganic non-metallic crystalline or partly crystalline, or glass, material that either solidifies upon cooling from a molten mass or that forms a solid structure due to the action of heat. There are innumerable examples of ceramic materials, all of which are intended to be within the scope of the present invention. Examples of ceramic materials include aluminum silicates, zirconium oxides such as zirconium dioxide, aluminum oxides, titanium oxides, tantalum oxides, carbides, borides, nitrites, and silicides, calcium ceramics such as calcium nitrite, calcium sulfate, calcium hydrogen sulfate, calcium hydroxide, calcium carbonates, calcium hydrogen carbonate, and calcium phosphates, alkali metal hydroxides, alkaline earth hydroxides, disodium hydrogen phosphate, disodium hydrogen phosphate dodecahydrate, disodium hydrogen phosphate heptahydrate, sodium phosphate dodecahydrate, dipotassium hydrogen phosphate, potassium phosphate tribasic, diammonium hydrogen phosphate, ammonium phosphate trihydrate, sodium bicarbonate, barium titanate, bismuth strontium calcium copper oxide, boron carbide, boron nitride, ferrite, lead zirconate titanate, magnesium diboride, silicon carbide, silicon nitride, steatite, uranium oxide, yttrium barium copper oxide, and zinc oxide.

As used herein, the term "ceramic article" refers to an article of manufacture that is made from a ceramic material. A ceramic article has a glazed or unglazed body of crystalline or partly crystalline structure, or of glass, which body is produced from essentially inorganic non-metallic substances and is either formed from a molten mass that solidifies upon cooling or is formed and simultaneously or subsequently matured by the action of heat.

As used herein the term "ceramic composition" refers to a composition composed of a ceramic material that flows sufficiently for casting purposes. The ceramic composition may be a solution or a non-solution and may be, for example, in the form of a melt, a slurry, or a flowable paste, which may be made by wetting a powder of a ceramic material with a liquid. The ceramic composition may contain additional components, such as binders, plasticizers, anti-flocculants, and lubricants.

The liquid of the fluid ceramic composition may be any liquid or multiplicity of liquids into which a ceramic material may be dispersed, with or without the use of additional materials such as a binder, plasticizer, anti-flocculant, or lubricant. The liquid may include additional additives such as a polymer, which may be water miscible or immiscible, and which may be hydrophilic, hydrophobic, or amphiphilic. Examples of suitable polymers include one or more of polypropylene (PP), amorphous polypropylene (APP), polyolefin (PL), polyethylene (PE), ethylene vinyl acetate (EVA), polystyrene (PS), polyvinyl acetate (PA), polyvinyl alcohol (PVA), polyphenylene oxide (PPO), polyethylene oxide (PEO), methyl cellulose (MC), carboxyl cellulose (CMC), hydroxyethyl cellulose (HEC), polyacrylate, apolyacrylamide, poly(lactide-co-glycolide) (PLGA), poly(lactide) (PLA), polyglycolic acid (PGA), polyanhydrides, poly(ortho ethers), polycarprolactone, polyethylene glycol (PEG), polyurethane, copolymers, polyacrylic acid, polyethylene glycol, polymethacrylic acid (PMMA), alginates, collagens, gelatins, hyaluronic acid, polyamides, polyvinylidene fluoride, polybutylene, and polyacrylonitrile.

The liquid of the fluid ceramic may be water miscible or immiscible and may be organic or inorganic solvents or solutes. One such liquid is water. Examples of polar organic solvents and solutes include alcohols such as methanol, ethanol, propanol, isopropanol, and butanol, carboxyl acids, sulfonic acids, compounds containing an —OH, —SH, enol, or phenol group, formic acid, 1,4-Dioxane, tetrahydrofuran, acetone, acetonitrile, dimethylformamide, and dimethyl sulfoxide. Examples of non-polar organic solvents and solutes include hexane, benzene, toluene, diethyl ether, chloroform, ethyl acetate, and dichloromethane. Examples of inorganic solutes are hydrobromic acid, hydrochloric acid hydroiodic acid, nitric acid, sulfuric acid, perchloric acid, boric acid, carbonic acid, chloric acid, hydrofluoric acid, phosphoric acid, pyrophosphoric acid, ammonium hydroxide, alkali metal hydroxide, alkaline earth hydroxide, disodium hydrogen phosphate, ammonia, methylamine, pyridine, disodium hydrogen phosphate, disodium hydrogen phosphate dodecahydrate, disodium hydrogen phosphate heptahydrate, sodium phosphate dodecahydrate, dipotassium hydrogen phosphate, potassium phosphate tribasic, diammonium hydrogen phosphate, ammonium phosphate, trihydrate, sodium bicarbonate, $NaHCO_3$, $NaHS$, $NaHSO_4$, $NaH_2PO_4$, $Na_2HPO_4$, $NH_4OH$, $NH_4H_2PO_4$, $(NH_4)_2HPO_4$, $NH_4HCO_3$, and $NH_4HSO_4$.

The fluid ceramic composition is formed into a desired shape by any method by which the desired shape may be formed. The desired shape may be any three-dimensional form. In order to make this form, the composition may be rolled, pulled, pressed, or molded to form a shape such as wire. The ceramic composition may be formed on a relatively planar surface or within a liquid, or may be cast upon an irregular non-planar template.

In many applications, it is desirable to obtain a porous ceramic article. Such products are useful for electrodes and supports for batteries and solid oxide fuel cells, for scaffolds for bone replacement and tissue engineering, for heating elements, for chemical sensors, for solar radiation conversion, and for filters in the steel industry. Porous ceramics may be are typically made by replica methods, using either a positive replica or a negative replica of the ceramic article.

With the positive replica technique, a porous template, such as a sponge, is coated with a fluid ceramic composition. The ceramic composition may or may not contain additives such as binders and plasticizers that provide strength and flexibility to the coating so that it will not crack during subsequent phases of the fabrication process. Following the coating step, the coated sponge is passed through rollers to remove the excess ceramic composition and to form a thin ceramic coating over the struts of the sponge. The ceramic coated sponge is then dried and pyrolysed by heating, typically between 300° and 800° C., which removes fluid from the ceramic composition, removes the replica template from the ceramic composition, and solidifies the ceramic composition. Finally, if desired, the remaining ceramic coating may be densified by sintering at temperatures ranging from 1100° to 1700° C. depending on the nature of the ceramic material.

The positive replica technique has a disadvantage for certain indications because the struts of a ceramic article made with this technique are necessarily hollow. This is because the ceramic composition coats portions of the template that define the struts. When the template is removed, this leaves a hollow ceramic strut overlying the space where the replica strut previously existed. Also, because of the removal of the porogen strut during pyrolysis, the ceramic struts often crack during this phase of manufacture, which markedly degrades the strength of the porous ceramic article.

The negative replica technique does not share these disadvantages. In this technique, a sacrificial porogen is utilized to make a template of the pores of a ceramic article, rather than of the product itself. According to this method, a negative replica of a desired porous ceramic article is made, typically by forming an assemblage of a multiplicity of discrete porogen elements, and casting a ceramic composition onto the assemblage and thereby obtaining a biphasic composition of a continuous matrix of the ceramic composition and a sacrificial phase within the matrix. The sacrificial phase may be distributed homogeneously throughout the ceramic matrix or may be assembled into a defined structure.

Following the formation of the biphasic composition, the matrix ceramic phase must be partially consolidated to form what is referred to as a "green body" or a "body" so that the porous structure of the ceramic composition does not collapse when the sacrificial porogen material is removed. Present methods of consolidation involve the use of setting agents or binders or the formation of a stiff attractive network of particles distributed throughout the matrix. Other methods include the use of sol-gel transitions based on the condensation of metal alkoxide and hydroxides in solution or by a curing process at a temperature slightly lower than that which will melt and remove the porogen materials.

The porogen materials are removed by a means that is selected based upon the nature of the porogen. Organic porogens, such as waxes, are often extracted by pyrolysis by applying long thermal treatments at temperatures between 200° and 600° C. Other sacrificial porogens, such as salts, ceramics, or metallic particles, are usually extracted by chemical leaching. Following the removal of the porogen, the ceramic is typically further processed, such as by kiln-firing or sintering.

Unlike the positive replica method, the negative replica method results in the formation of a ceramic article having struts that are solid, rather than hollow. Therefore, the negative replica method produces porous templates that typically have a higher compressive strength than do ceramic articles of similar porosity formed by the positive replica method.

Another advantage of the negative replica method is that it provides precise control over the architecture of the ceramic articles and can be used to produce products that are graded, either functionally or structurally. For example, gradations of pore size within a ceramic article may be obtained by grading the distribution of porogen particles of various sizes within the negative replica. In addition, gradations of composition with a ceramic article may be obtained by grading the distribution of ceramic slurry within the negative replica.

In both the positive and negative replica method, the template may be made of any material upon which a ceramic composition may be cast and which can be removed by a method that does not destroy the structure of the resulting ceramic article. Positive templates are typically made of a polymeric sponge, such as polyurethane. Other positive template materials include carbon foam and natural templates such as coral and wood. Negative template porogens include polymers such as poly(lactide) or poly(lactide-co-glycolide), salts, sugars, and waxes such as paraffin.

The method of the present invention is applicable to any method for forming a ceramic article, including methods as indicated above in which no template is used and those in which a template is used. If a template is used in the formation of a ceramic article, the method is applicable to both positive and negative replica template methods.

According to the method of the invention, a hardening step is performed prior to the final curing step of a ceramic article. With non-template methods of forming a ceramic article, such as when making an essentially non-porous ceramic article, the hardening step is performed before the ceramic composition has solidified and while it is still pliable. With template methods of forming a ceramic article, the hardening step is preferably performed prior to removal of the positive or negative template from the ceramic composition. Thus, with negative template methods, the hardening step is preferably performed during the formation of the green body. Because it is desirable that the ceramic composition should be as hard as possible before the template is removed, so as to minimize the occurrence of cracks in the composition, it is not preferred, although it is possible and is within the scope of the present invention, to perform the hardening step of the invention after the template has been removed from the ceramic composition.

In accordance with the invention, the hardening step is performed by exposing the ceramic composition to a liquid extraction solvent in which the non-fluid components of the ceramic composition are practically insoluble or are insoluble and in which the fluid component of the ceramic composition is miscible for a time sufficient to remove fluid from the ceramic composition. The amount of time in which the ceramic composition is exposed to the liquid extraction solvent may be varied, depending on several factors, including the materials comprising the ceramic composition, the fluid component of the in the ceramic composition, the liquid extraction solvent employed, and the degree of hardening that is desired. Typically, but not necessarily, the hardening step is performed for a time sufficient that the ceramic composition will be sufficiently hard to maintain its structural integrity in the absence of external support, for example as shown in FIG. 1. In the situation where a ceramic composition is combined with a template, the material composing the template is preferably, but not necessarily, practically insoluble or insoluble in the solvent so as not to remove the support of the template from the ceramic composition before the ceramic composition has hardened. If the template material is soluble to some extent in the solvent, then the amount of time that the template is exposed to the solvent should be adjusted so that the strength of the template is not reduced by dissolution to an extent that the ceramic composition is no longer sufficiently supported.

The selection of the particular extraction solvent employed will depend on the identities of the fluid contained within the ceramic composition and of the composition of the template if present. For example, if the ceramic composition fluid is water, optionally containing a binder such as carboxymethyl cellulose (CMC), and the template is composed of paraffin, a preferred extraction solvent is a short-chain alkyl or aryl alcohol, such as methanol, ethanol, isopropanol, butanol, or phenol, or a mixture thereof. For another example, if the ceramic composition fluid is acetone, optionally containing a binder such as polymethyl methacrylate (PMMA), and the template is composted of sugar or salt, a suitable extraction solvent may be one or more of tetrahydrofuran (THF), hexane, benzene, or toluene.

The ceramic composition, and the template if present, should be immersed in the extraction solvent at a temperature below the melting point of the template. Because paraffin typically melts between 47° and 64° C., it is preferred that, if paraffin is the material of which the template is composed, the temperature of the extraction solvent should be less than 50°, more preferably less than 47°, and most preferably less than 45° C.

The concentration of the extraction solvent should be that which is sufficient to cause removal of fluid from the ceramic composition. In the situation where the ceramic composition fluid is water, a preferred concentration of ethanol is 70%. This concentration of ethanol has been found to extract water from a ceramic concentration sufficiently to increase the hardness and strength of the resulting ceramic article. If desired, a higher concentration of ethanol may be used, but care should be utilized to ensure that the ceramic composition fluid is not removed so rapidly to crack or deform or otherwise result in structural weakness of the ceramic article.

In one especially preferred embodiment, the fluid in the ceramic composition, with or without an associated positive or negative template, is extracted by exposing the composing to sequentially higher concentrations of the extraction solvent. The stepwise increase in extraction solvent concentration is preferred because a high concentration of the solvent may be utilized in this fashion which more efficiently dissolves fluid from the ceramic composition but does not dissolve the fluid as rapidly as if the ceramic composition had been exposed immediately to the higher concentration of solvent. Thus, the graded drying reduces the potential stress on the ceramic composition due to an overly rapid drying process.

For example, if the extraction solvent is ethanol, the ceramic composition, with or without an associated template, may first be exposed to the ethanol at a concentration of 70%. The ceramic composition may then be removed from the ethanol and then exposed to ethanol at a concentration of 80%. Alternatively, 95% ethanol could be added to the ethanol that the ceramic composition is in so as to raise the concentration to 80%. Following the extraction with 80% ethanol, further extraction may be performed with 90% ethanol and/or with 95% ethanol. Similar extraction procedures may be used with other combinations of ceramic composition fluid and extraction solvent.

If desired, the extraction fluid may also be utilized to remove a template, such as a sacrificial porogen utilized as a negative replica. By immersing a ceramic composition and replica template in an extraction fluid at a temperature higher than the melting point of the material of which the template is composed, the template will liquefy and will flow out of the ceramic composition and into the extraction fluid. For example, with paraffin as a template, ethanol or other alcohol may be used at a temperature above the melting point of paraffin, which is typically 50° C. or higher.

It is preferred that the extraction fluid utilized be one in which the material of the replica template is not soluble. In this way, the extraction fluid and the liquified template will remain in separate phases and can readily be separated from each other. This will allow for easy collection of the template material from the extraction fluid which will allow for both the extraction fluid and the replica template material to be recycled and reused. Removal of the template material in this manner also obviates the need for pyrolysis, burning out the porogen at very high temperatures, which may potentially cause structural defects such as microcracks and therefore reduce the mechanical strength of the ceramic article.

In a preferred embodiment, the extraction of fluid from the ceramic composition is performed utilizing a solvent in which a template material is not soluble at a temperature below that of the melting point of the template material and then the temperature of the extraction fluid is elevated to that above the melting point of the template material during continued fluid extraction. In this way, strengthening of the ceramic composition and removal of the template is performed in a single process.

For example, if a paraffin positive or negative replica template is utilized in the fabrication of a ceramic article, the ceramic composition associated with the template may be exposed to 70% ethyl alcohol at a temperature below the melting point of paraffin. This temperature is maintained for a sufficient time to ensure that, when the template is removed, the ceramic composition will be sufficiently strong not to collapse if the paraffin were to be removed. The temperature of the ethyl alcohol may then be increased to a temperature above the melting temperature of the paraffin, which will cause the paraffin to melt. The ethyl alcohol and paraffin may be removed and replaced with successive treatments of higher concentration ethyl alcohol for further extraction of fluid from the ceramic composition, which is now a green body.

The composition of the invention is a solvent-hardened ceramic article, that is the article was made by a process in which a liquid-containing ceramic composition is formed into a desired shape and is exposed to a solvent in which the liquid contained in the ceramic composition is soluble at a concentration and for a time sufficient to extract the liquid from the composition and that following the extraction, the "dried" composition, which is preferably completely free of liquid, is caused or permitted to solidify to form the ceramic article.

The ceramic article made by the method of the invention may be non-porous or porous. If porous, it may be made by any method by which a porous ceramic article may be made so long as the ceramic composition is subjected to the solvent extraction step prior to the final solidification of the composition to form the ceramic article. The porous ceramic article may be made with any desired degree of porosity, from 1% to over 90%. For example for calcium phosphate, as well as other ceramic articles, the porosity may be between 60% and 95%, preferably between 70% and 90%. The porous ceramic articles of the invention may be made to have any desired degree of interconnectivity between pores, up to 100% interconnectivity. The porous ceramic article may be made by a negative replica method in which discrete porogen particles are used to define a template upon which a ceramic composition is cast. One advantage of the negative replica method is that the interconnectivity of the pores may be controlled by heating or otherwise causing individual elements of the sacrificial porogen to coalesce to a desired degree which will correspond to the degree of interconnectivity of pores in the final ceramic article. Another advantage of the negative replica method is that the solvent-hardened ceramic article of the invention may be a porous article having uniformity of distribution of pores, pore sizes, and composition or any of these characteristics of the article may be varied to provide a porous article that varies spatially in the distribution of pores, of pore sizes, and/or of composition. Non-porous articles of the invention may also be compositionally graded.

The ceramic articles produced by the method of the invention have many uses. The increased compressive strength of the ceramic articles of the invention will prove of use in many fields, including for structural materials for buildings and electronics, as well as for making biodegradable ceramic articles for implantation into the body of humans and other animals. One particular use of the ceramic articles of the invention is for the implantation in order to repair bone. Synthetic biodegradable ceramic bone graft materials made by presently available methods of manufacture have compressive strength less than that of bone. Additionally, the ceramic bone graft materials lose a significant portion of their initial strength over time as the synthetic bone is absorbed into the body. The method of the present invention, utilized for strengthening biodegradable ceramic bone grafts, therefore will provide a significant contribution to this field.

The method of the invention is useful in the creation of macroporous structures which have a high degree of interconnectivity between pores and a high compressive strength. The method of the invention has been utilized in making a sintered macroporous CaP ceramic article by a negative replica method, which articles may have 100% interconnectivity between pores, a porosity up to or even higher than 70%, and solid struts between pores. The inventors had found that similar articles produced by prior art negative replica methods lacking the solvent extraction step of the present invention were not sufficiently strong to withstand sintering temperatures. In fact, to the knowledge of the inventor, no macroporous article made by negative replica methods and having 100% interconnectivity between pores has been produced prior to the present invention.

To further illustrate the invention, the following examples are provided. It is to be understood that these examples are provided for illustrative purposes and are not to be construed as limiting the scope of the invention.

EXAMPLE 1

Paraffin beads were prepared by a conventional water-suspension method. The paraffin beads were sifted in order to obtain beads with diameters ranging from 1.2 to 1.8 mm. The sifted beads were filled into polyethylene cylinder tubes. The filled tubes were placed into warm water at a temperature of about 50° C. to allow the beads to soften and to coalesce into a unitary mold structure.

A fine tricalcium phosphate (TCP) powder (Nanocerox, Ann Arbor, Mich.) was mixed with distilled water at various weight ratios of 1:(0.2~10). This mixture was stirred and carboxymethyl cellulose (CMC) was added at various weight ratios of 1:(20~1). The mixtures were stirred until a homogenous slurry was obtained.

The slurry was poured onto the top of the paraffin mold. The mold with the slurry was placed into a vacuum chamber for at least 10 minutes, at which time the chamber was filled with air and the paraffin mold was checked to determine if it had been completely filled with the slurry. If not, additional repetitions of the pouring of the slurry onto the mold and the exposure to the vacuum were performed until it was determined that the paraffin mold was completely cast with the slurry to make porous ceramic bodies for making macroporous ceramic articles.

Another set of samples was prepared by directly filling the slurry into the polyethylene cylinder tubes, without prior filling of the tubes with paraffin beads. These molds, which were not cast upon a negative template, in order to make solid (non-porous) ceramic bodies for making nonporous ceramic articles, referred to below as scaffolds.

The ceramic bodies, porous and non-porous, were soaked in 70% ethyl alcohol at a temperature between 30° and 60° C. for at least 30 minutes. The temperature was then increased to between 60° and 100° C. and maintained for no less than 30 minutes in order to melt and remove the paraffin molds. The alcohol and melted paraffin were removed and replaced with 80% to 95% ethyl alcohol at 60° to 100° C. and maintained for at least 30 minutes. The ethyl alcohol was changed and replaced with new ethyl alcohol at the same concentration and maintained for at least 30 minutes.

A control group for each of the solid and porous ceramic bodies was air dried, without applying this solvent-based solidifying and drying fluid extraction process.

All of the samples were then placed into an electric furnace and were heated to a temperature of 1100° to 1300° C. for a period of 3 hours to produce sintered porous and non-porous ceramic articles.

EXAMPLE 2

Testing of the Ceramic Articles of Example 1

The porosity of the porous ceramic scaffolds was calculated by dividing the apparent density of the scaffold with the TCP theoretical density of 3.14 g/cm$^3$ and was determined to be about 73%. The apparent density of the scaffolds were determined by measuring the mass of the scaffold and dividing by its volume. Macromorphology and three-dimensional structure of the scaffolds were determined by Micro CT (MicroCAT™ II, Imtek Inc., Knoxyille, Tenn.). Scanning electron microscopy (JSM-840A, JEOL USA, Inc., Peabody, Mass.) was used to determine the microstructure of the scaffolds. Maximum compressive strength of the ceramic articles prepared in Example 1 was tested by using a screw-driven testing machine (Instron 4465, Instron Corp., Canton, Mass.).

The maximum compressive strength was measured and, for a macroporous scaffold made with the solvent extraction step, having 100% connectivity and having pore sizes of 350-500 µm and 600-800 µM, was determined to be 17+/−4 MPa. It was not possible to determine the compressive strength of the similar macroporous scaffold made without the solvent extraction step, because these scaffolds invariably cracked into pieces prior to or during the exposure to sintering temperatures. FIG. 1 shows, on the left side, a plastic tube filled with a slurry of a ceramic composition prior to drying, in the middle, a macroporous green body dried by the solvent-extraction method of the invention, and on the right side, a green body dried by exposure to air at room temperature. As shown in the middle of FIG. 1, the solvent extraction drying step maintained the integrity of the green body whereas, as shown in the right side of FIG. 1, air drying did not maintain the integrity of the green body, which crumbled and cracked into a multiplicity of pieces.

Similarly, maximum compressive strength of a dense non-porous article of Example 1 was determined to be 297.8+/−73.0 MPa. The comparable dense non-porous articles made without the hardening step of the invention invariably developed cracks during sintering and so were not tested for compressive strength.

This example establishes that ceramic articles, either porous or non-porous, may be made by the method of the invention and that such ceramic articles are able to withstand treatment such as by sintering. Moreover, such articles have very high compressive strength.

EXAMPLE 3

Comparison of Strength of Macroporous Scaffolds

The compressive strength of additional macroporous CaP scaffolds made according to the method of Example 1 and having a porosity of 73% was tested by the method of Example 2 and determined to be 16.86 MPa+/−3.60 MPa. This was compared to the strength of prior art macroporous scaffolds made with various methods as reported in the scientific literature. See, Hing, J. Mater. Sci. Mater. Med., 10(3): 135-145 (1999); Liu, Ceramics International, 23:135-139 (1997); Seplveda, J. Biomed. Mater. Res., 50:27-34 (2000); Ramay, Biomaterials, 24:3293-3302 (2003); Almirall, Biomaterials, 25:3671-3680 (2004); Cyster, Biomaterials, 26:697-702 (2005); Silva, Biomaterials, 27:5909-5917 (2006); Uemura, Biomaterials, 24:2277-2286 (2003); Sous, Biomaterials, 19:2147-2153 (1998); Guo, Tissue Engineering, 10:1830-1840 (2004); Kwon, J. Am. Ceramic Soc., 85:3129-3131 (2002); and Milosevski, Ceramics International, 25:693-696 (1999). The results are shown in FIG. 2, which is a graph plotting compressive strength in MPa on the Y-axis and porosity in volume % on the X-axis.

Figure 2:
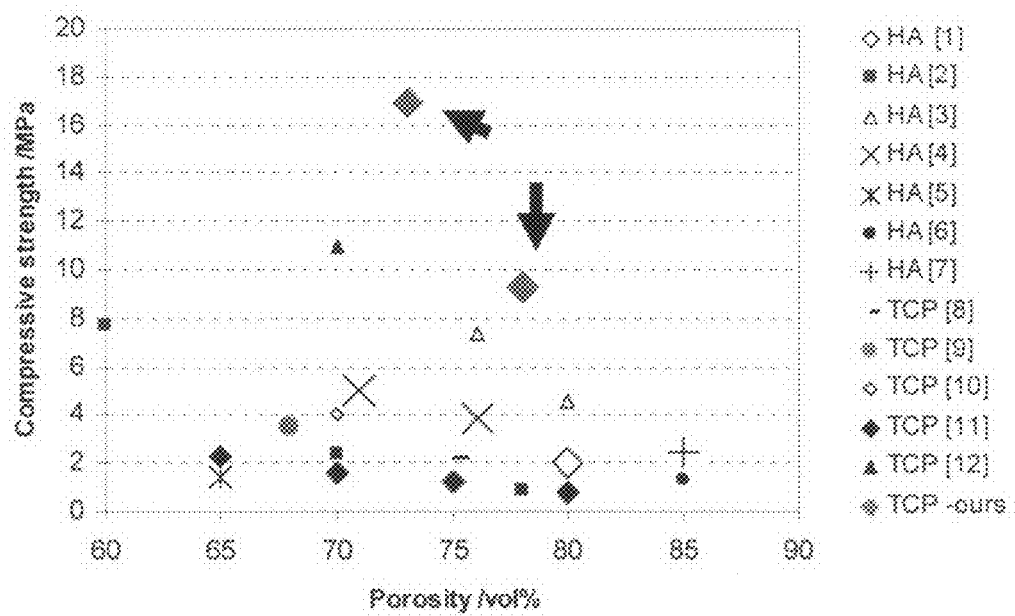
FIG. 2 is a graph comparing the compressive strength in MPa of a porous ceramic article made by the method of the invention with porous ceramic articles made by methods other than that of the invention. The arrows point to data points for the porous ceramic articles made by the method of the invention.

As shown in FIG. 2, the compressive strength of the macroporous scaffold made according to the invention (indicated by the arrow) is markedly higher than is that of prior art scaffolds made in different ways. This is true even for scaffolds of lower porosity which, because of higher mass per volume, should be stronger than higher porosity scaffolds.

EXAMPLE 4

Compressive Strength of Cortical Bone and Biomimetic CaP Scaffold

Figure 3:
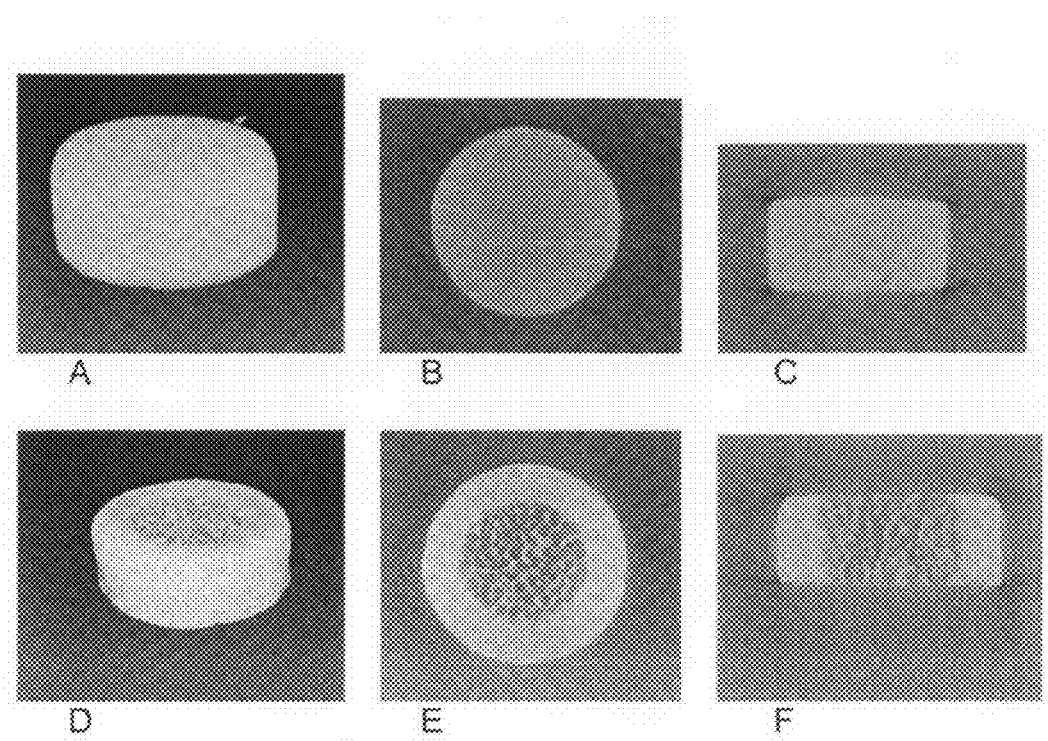
FIG. 3A is a 3-dimensional computer-reconstructed Micro CT (coaxial tomographic) image of a dense scaffold showing the lack of pores made to mimic the structure of cortical bone.
FIG. 3B is a top view 2-dimensional Micro CT image of the dense scaffold.
FIG. 3C is a side view 2-dimensional Micro CT image of the dense scaffold.
FIG. 3D is a 3-dimensional computer-reconstructed Micro CT image of a two-zone graded ceramic scaffold having pores in the inner zone and lacking pores in the outer zone made to mimic the structure of bone.
FIG. 3E is a top view 2-dimensional Micro CT image of the graded scaffold.
FIG. 3F is a side view 2-dimensional Micro CT image of the graded scaffold.

A dense CaP ceramic article, referred to in this example as a scaffold even though the article lacks pores, was made according to Example 1. FIG. 3A-C is a 3-dimensional and two 2-dimensional Micro CT (coaxial tomographic) images of dense scaffold showing the lack of pores. This pore-less scaffold was made to mimic the structure of cortical bone.

A graded CaP ceramic scaffold, containing an outer zone of dense pore-less ceramic and an inner zone of a porous scaffold, was made according to Example 1. FIG. 3D-F is a 3-dimensional and two 2-dimensional MicroCT images of the scaffold showing the two-zone graded ceramic scaffold having 600 µm to 800 µm pores in the inner zone and lacking pores in the outer zone. This two-zone scaffold was made to mimic naturally occurring bone having an inner zone of cancellous bone and an outer zone of cortical bone. The two-zone graded ceramic scaffold was made by filling a tube with paraffin beads followed by filling of the tube with a ceramic slurry and filling an outer concentric tube with the slurry without first filling the tube with the beads.

The compressive strength of the dense ceramic scaffold and the two-zone ceramic scaffold was determined as described in Example 2 and was compared to the strength of cortical bone reported in An Y H and Draughn, R A, "Mechanical Testing of Bone and the Bone-Implant Interface", CRC Press, Boca Raton, Fla. (2000).

The strength of cortical bone reported in An and Draughn is 120+/−35 MPa. The strength of the non-porous dense CaP scaffold was determined to be 297.8+/−73.0 MPa. The strength of the two-zone scaffold, mimicking the structure of bone having both cortical and cancellous zones, was determined to be 153.9+/−29.2 MPa.

The results of this study were surprising because, not only was the compressive strength of the dense scaffold substantially higher than that of cortical bone, the two-zone scaffold also had a compressive strength similar to or somewhat higher than that of cortical bone. It is to be noted that the compressive strength of bone having both cortical and cancellous portions will naturally be less than that of cortical bone alone.

Therefore, the data establish that the CaP scaffold made by the method of the invention has a strength that is equal to or higher than that of bone. This indicates that the scaffolds of the invention should be able to withstand functional loading when used as implants for long bone grafting.

EXAMPLE 5

Manufacture of Macroporous Scaffold

Figure 4:
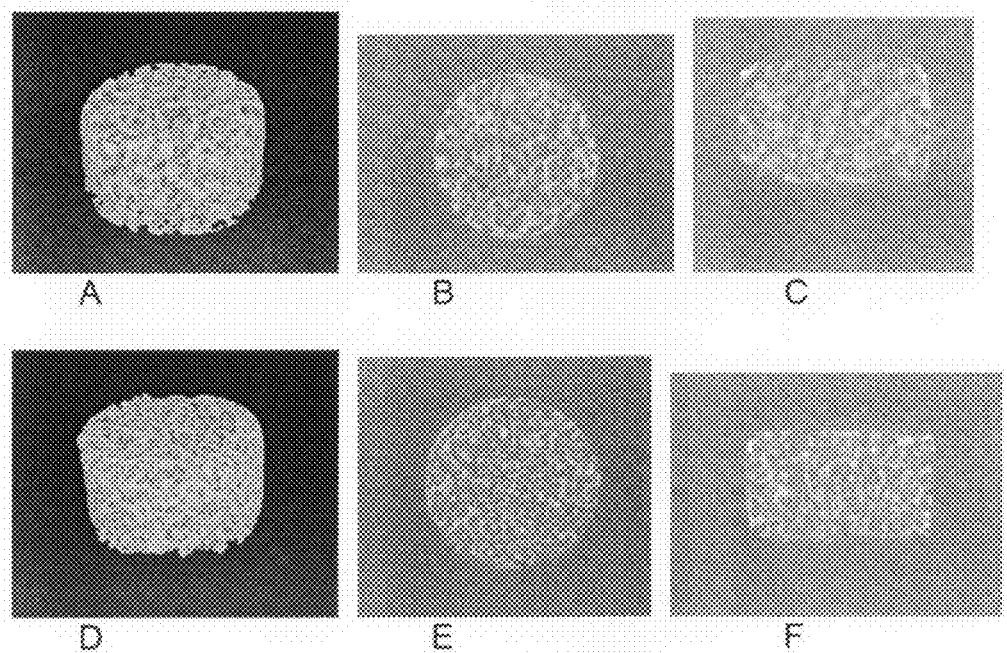
FIG. 4A is a 3-dimensional computer-reconstructed Micro CT image of a porous scaffold with pores of 600 μm to 800 μm.
FIG. 4B is a top view 2-dimensional Micro CT image of the porous scaffold.
FIG. 4C is a side view 2-dimensional Micro CT image of the porous scaffold.
FIG. 4D is a 3-dimensional computer-reconstructed Micro CT image of a porous scaffold with pores of 350 μm to 500 μm.
FIG. 4E is a top view 2-dimensional Micro CT image of the porous scaffold.
FIG. 4F is a side view 2-dimensional Micro CT image of the porous scaffold.

Macroporous scaffolds were made according to Example 1 to produce scaffolds of homogenous pore structure having pores between 600 µm to 800 µm, shown in FIGS. 4A-C, and between 350 µm and 500 µm, shown in FIGS. 4D-F.

EXAMPLE 6

Interconnection of Pores of Macroporous Scaffold

Figure 5:
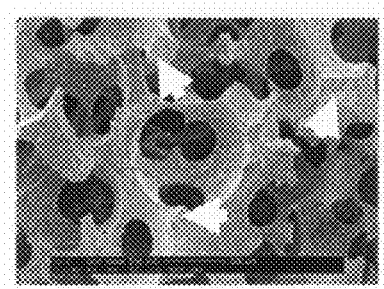
FIG. 5 is a scanning electron microscopy photograph showing the solid struts and interconnectivity between pores of a scaffold made by a negative replica method. The arrows indicate the solid struts.

A macroporous scaffold having pores between 600 µm to 800 µm was made according to Example 1 and was imaged by scanning electron microscopy, as shown in FIG. 5. The interconnective pore size was determined to be 440+/−57 μm. The struts between pores are solid due to formation of the scaffold by the negative replica method.

EXAMPLE 7

Manufacture of Radially Graded Macroporous Scaffold

Figure 6:
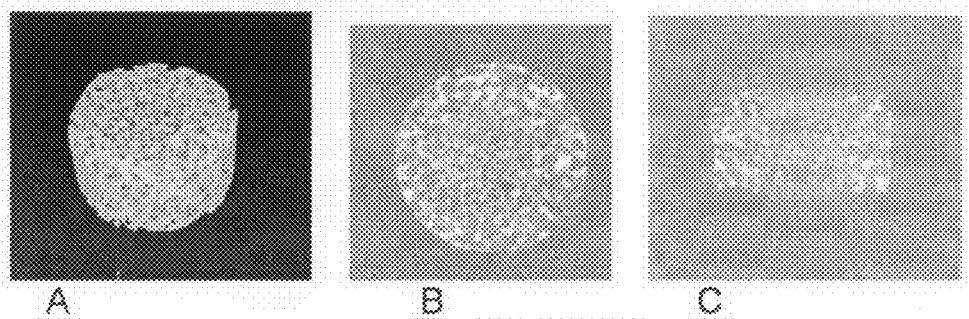
FIG. 6A is a 3-dimensional computer-reconstructed Micro CT image of a radially graded porous ceramic article in which an inner zone of the article contains pores between 350 µm to 500 µm in diameter and an outer zone contains pores between 600 µm and 800 µm.
FIG. 6B is a top view 2-dimensional Micro CT image of this radially graded porous ceramic article.
FIG. 6C is a corresponding MicroCT side image.
Figure 7:
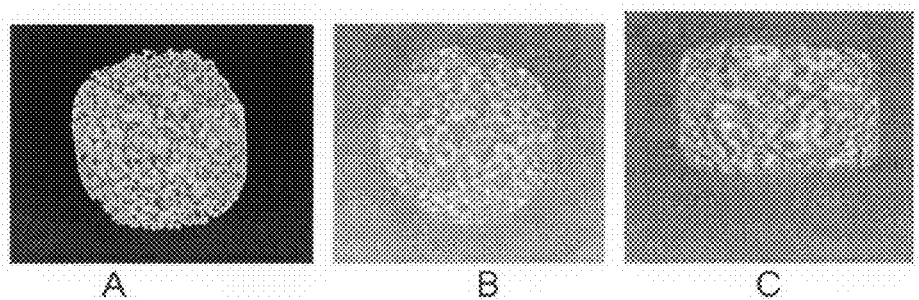
FIG. 7A is a 3-dimensional computer-reconstructed Micro CT image of a radially graded porous ceramic article in which an inner zone of the article contains pores between 600 µm and 800 µm in diameter and an outer zone contains pores between 350 µm to 500 µm in diameter.
FIG. 7B is a 2-dimensional Micro CT top to bottom image of this radially graded porous ceramic article.
FIG. 7C is a corresponding 2-dimensional Micro CT side image.

Macroporous scaffolds were made according to Example 1 except that two concentric polyethylene tubes were utilized and paraffin beads of two different sizes were respectively filled into each of the tubes. FIG. 6A-C shows a 3-D and two 2-D Micro CT images of a radially graded porous ceramic article in which an inner zone of the article contains pores between 350 μm to 500 μm in diameter and an outer zone contains pores between 600 μm and 800 μm. FIG. 7D-F shows a 3-D and two 2-D Micro CT images of a radially graded porous ceramic article in which an inner zone of the article contains pores between 600 μm and 800 μm in diameter and an outer zone contains pores between 350 μm to 500 μm in diameter.

EXAMPLE 8

Manufacture of Vertically Graded Macroporous Scaffold

Figure 8:
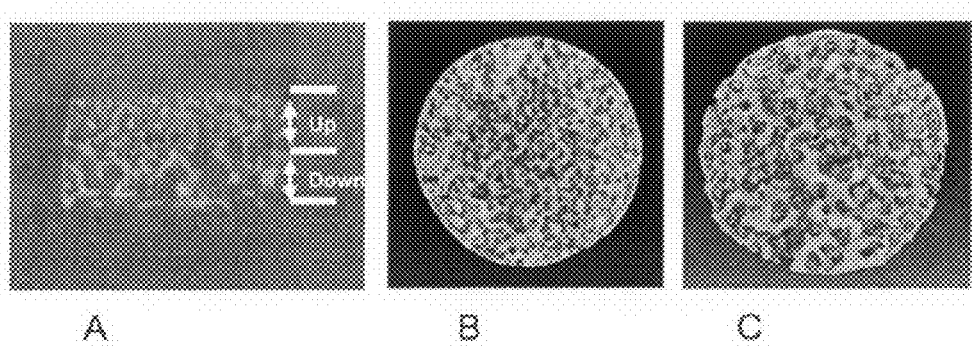
FIG. 8A is a 2-dimensional Micro CT side image of a vertically graded macroporous ceramic article in which the top portion has smaller pores of 300 µm to 400 µm and the bottom portion has larger pores of 600 µm to 700 µm.
FIG. 8B is a top view 3-dimensional computer-reconstructed Micro CT image of the vertically graded macroporous article showing the smaller pores at the top surface.
FIG. 8C is a bottom view 3-dimensional computer-reconstructed Micro CT image of the article showing the larger pores at the bottom surface.

A macroporous scaffold was made according to Example 1 except that two differently sized populations of paraffin beads were sequentially used to fill the polyethylene tube. FIG. 8A-C shows a 2-dimensional Micro CT image of the resultant vertically graded macroporous structure in which the top portion has smaller pores of 300 μm to 400 μm and the bottom portion has larger pores of 600 μm to 700 μm, a top view 3-dimensional Micro CT image of the vertically graded macroporous structure showing the smaller pores at the top surface, and a bottom view 3-dimensional Micro CT image of the structure showing the larger pores at the bottom surface.

EXAMPLE 9

Manufacture of Compositionally Graded Macroporous Scaffold

Figure 9:
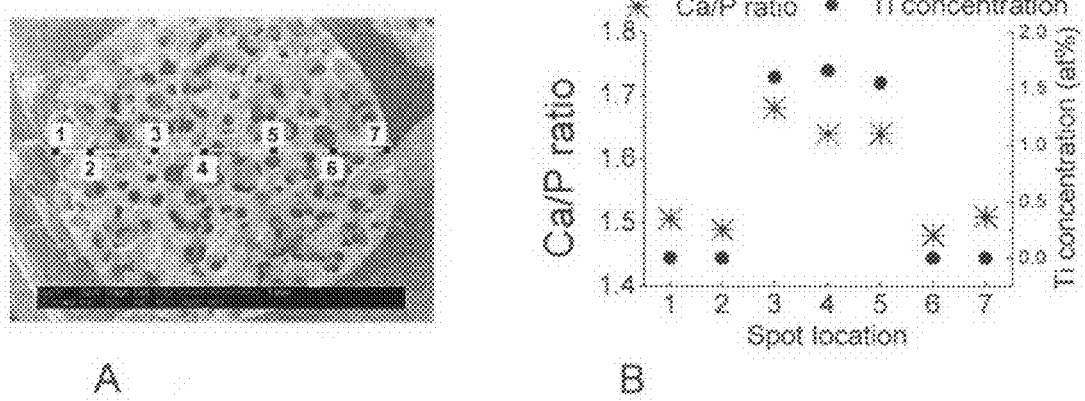
FIG. 9A is a scanning electron microscopy photograph of a compositionally graded porous ceramic article.
FIG. 9B is a graph that indicates the varying composition of the article at various numbered locations as shown in FIG. 9A.

A macroporous scaffold was made according to Example 1 except that two concentrically arranged polyethylene tubes were utilized and different compositions of ceramic material were poured into each tube. The centrally positioned tube contained a ceramic material that was relatively hydroxyapatite (HA) enriched, had a calcium/phosphorus (Ca/P) ratio of about 1.64-1.68:1, and contained titanium oxide. The peripherally positioned tube contained a ceramic material that was relatively tricalcium phosphate (TCP) enriched, had a Ca/P ratio of about 1.48-1.51:1, and did not contain titanium oxide. FIG. 9a shows selected measurement spots in the scaffold. FIG. 9b shows the varying compositions of the scaffold at each measurement spot.

As shown in FIG. 9b, the Ca/P ratio was higher, between 1.64-1.68:1, in the central HA enriched area of the scaffold compared to between 1.48-1.51:1 in the peripheral areas of the scaffold. Additionally, higher concentrations of titanium, 1.55-1.66 at %, were present in the peripheral area and the amount of titanium in the peripheral areas was at or about zero. This study established that there was little movement of slurry components during the template-casting procedure and that the method of the invention may be used to produce compositionally graded ceramic articles.

While preferred embodiments of the invention have been described in detail, it will be apparent to those skilled in the art that the disclosed embodiments may be modified. It is intended that such modifications be encompassed in the following claims. Therefore, the foregoing description is to be considered to be exemplary rather than limiting, and the scope of the invention is that defined by the following claims.

The invention claimed is:

1. A method for making a ceramic article, comprising:
    obtaining a ceramic composition containing a fluid,
    forming the ceramic composition into a desired shape, wherein said forming comprises casting the ceramic composition onto a negative replica comprising a sacrificial porogen, said porogen having a defined melting point and being insoluble in a first concentration of a liquid solvent below said defined melting point,
    sequentially exposing the shaped ceramic composition to increasing concentrations of the liquid solvent in which the fluid contained in the ceramic composition is soluble, said sequentially exposing comprising:
        following a first exposure to the first concentration of said liquid solvent at a temperature below said defined melting point, exposing said shaped ceramic composition to said first concentration or a second, higher concentration of said liquid solvent at an increased temperature at or above the defined melting point, and
        exposing said shaped ceramic composition to a subsequent, higher concentration of said liquid solvent at a temperature at or above the defined melting point,
        thereby removing said fluid from the ceramic composition, removing said negative replica and hardening the shaped ceramic composition, and
    solidifying the ceramic composition to obtain a ceramic article having a maximum compressive strength greater than that of the same ceramic article made without said sequential exposure of the shaped ceramic composition to increasing concentrations of said liquid solvent and said temperature increase.

2. The method of claim 1 wherein the said fluid comprises water.

3. The method of claim 1 wherein the shaped ceramic composition is porous.

4. The method of claim 1 wherein said sacrificial porogen is not soluble in said first concentration of the liquid solvent at said temperature below said defined melting point, and wherein said sacrificial porogen is melted by said first concentration or said second, higher concentration of said liquid solvent, at said increased temperature at or above the defined melting point, and wherein said sacrificial porogen is further melted by said subsequent, higher concentration of said liquid solvent at said increased temperature at or above said defined melting point, to remove said negative replica.

5. The method of claim 1 wherein the sacrificial porogen comprises a multiplicity of discrete elements.

6. The method of claim 5 wherein the elements of the sacrificial porogen are organized into zones that differ based on porogen size.

7. The method of claim 1 wherein the sacrificial porogen is selected from the group consisting of waxes, gelatins, naphthalene, and polymers.

8. The method of claim 1 wherein the sacrificial porogen is paraffin.

9. The method of claim 8 wherein the liquid solvent is alcohol.

10. The method of claim 9 wherein the alcohol is ethanol.

11. The method of claim 1 wherein the ceramic composition comprises a calcium phosphate ceramic material.

12. The method of claim 11 wherein the calcium phosphate is hydroxyapatite, tricalcium phosphate, or a mixture of hydroxyapatite and tricalcium phosphate.

13. The method of claim 1 wherein said first exposure comprises exposing the ceramic composition to a 70% concentration of the liquid solvent.

14. The method of claim 1, wherein said sequentially exposing comprises, following said first exposure to the first concentration of the liquid solvent at a temperature below said defined melting point, increasing the temperature of said first concentration of liquid solvent to a temperature at or above the defined melting point, and subsequently exposing said shaped ceramic composition to said subsequent, higher concentration of said liquid solvent at or above said defined melting point, thereby removing said fluid from the ceramic composition, removing said negative replica, and hardening the shaped ceramic composition.

15. The method of claim 1, wherein said sequentially exposing comprises, following the first exposure to the first concentration of said liquid solvent at a temperature below said defined melting point, exposing said shaped ceramic composition to a second, higher concentration of said liquid solvent at an increased temperature at or above the defined melting point, and then exposing said shaped ceramic composition to a subsequent, higher concentration of said liquid solvent at a temperature at or above the defined melting point, thereby removing said fluid from the ceramic composition, removing said negative replica, and hardening the shaped ceramic composition.

16. The method of claim 1, comprising separating a melted porogen phase from a liquid phase containing said liquid solvent and said extracted fluid, and recovering the melted porogen phase for making another negative replica.

* * * * *